United States Patent
Walker (12)

(10) Patent No.: US 6,375,727 B1
(45) Date of Patent: Apr. 23, 2002

(54) AMINE OXIDE/IODINE CONTAINING BLENDS FOR WOOD PRESERVATION

(75) Inventor: Leigh E. Walker, Macungie, PA (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/577,330

(22) Filed: May 24, 2000

Related U.S. Application Data

(60) Provisional application No. 60/135,568, filed on May 24, 1999.

(51) Int. Cl.$^7$ ............................................... A01N 33/02
(52) U.S. Cl. .................... 106/18.32; 106/2; 106/18.35; 514/228.8; 514/231.2; 514/75; 514/478; 514/479; 514/644; 514/672
(58) Field of Search ................ 106/2, 15.05, 18.32, 106/18.35; 514/228.8, 231.2, 478, 479, 644, 672, 75

(56) References Cited

U.S. PATENT DOCUMENTS

| | | | |
|---|---|---|---|
| 3,296,145 A | 1/1967 | Findlan et al. .............. | 252/106 |
| 3,484,523 A | 12/1969 | Findlan et al. .............. | 424/248 |
| 3,761,488 A | 9/1973 | Lewis et al. ................ | 260/302 |
| 4,005,193 A | 1/1977 | Green et al. ................ | 424/168 |
| 4,105,431 A | 8/1978 | Lewis et al. .................... | 71/67 |
| 4,357,163 A | * 11/1982 | Amundsen et al. ...... | 106/18.35 |
| 4,379,710 A | 4/1983 | Amundsen et al. ......... | 428/541 |
| 4,382,105 A | 5/1983 | Amundsen et al. ......... | 427/370 |
| 4,622,248 A | 11/1986 | Leach et al. ................ | 427/440 |
| 4,857,322 A | 8/1989 | Goettsche et al. .......... | 424/633 |
| 4,929,454 A | 5/1990 | Findlay ...................... | 424/638 |
| 4,937,143 A | 6/1990 | West ........................ | 427/419.8 |
| 4,950,685 A | 8/1990 | Ward .......................... | 514/479 |
| 5,073,570 A | 12/1991 | Tseng .......................... | 514/533 |
| 5,276,029 A | 1/1994 | Goettsche et al. ....... | 514/231.2 |
| 5,304,237 A | 4/1994 | Barth et al. ................ | 106/18.3 |
| 5,426,121 A | 6/1995 | Bell ............................ | 514/500 |
| 5,468,284 A | 11/1995 | Sturm ........................... | 106/2 |
| 5,527,384 A | 6/1996 | Williams et al. ......... | 106/18.32 |
| 5,536,505 A | 7/1996 | Yu ........................... | 106/18.33 |
| 5,582,869 A | * 12/1996 | Yu ............................... | 427/297 |
| 5,833,741 A | * 11/1998 | Walker ......................... | 106/2 |
| 5,858,921 A | 1/1999 | Magin et al. ............... | 504/206 |
| 6,180,672 B1 | 1/2001 | Lichtenberg et al. ....... | 514/561 |
| 6,197,805 B1 | * 3/2001 | Smith ......................... | 514/388 |

FOREIGN PATENT DOCUMENTS

| | | | | |
|---|---|---|---|---|
| CA | 1 174 005 | | 9/1984 | .......... A01N/31/14 |
| DE | 3743 821 A1 | | 7/1989 | ............ B27K/3/34 |
| DE | 4217 882 A1 | | 12/1993 | .......... A01N/55/04 |
| DE | 44 41 674 A1 | | 5/1996 | ......... C07C/275/32 |
| DE | 196 40 874 | | 4/1998 | ............ B27K/3/34 |
| DE | 196 48 888 A1 | | 5/1998 | ............ B27K/3/50 |
| EP | 0 370 182 | | 5/1990 | ............ B27K/3/50 |
| EP | 0 381 482 | | 8/1990 | ............ B27K/3/50 |
| EP | 0 571 846 A1 | | 12/1993 | .......... A01N/47/12 |
| JP | 57022003 | | 2/1982 | ............ B27K/3/52 |
| JP | 64-1796 | | 1/1989 | ............ C11D/3/28 |
| JP | 1-268605 | | 10/1989 | .......... A01N/33/24 |
| WO | 93/24012 | * | 12/1993 | |
| WO | 97/01423 | | 1/1997 | ............ B27K/3/50 |
| WO | 98/00008 | | 1/1998 | .......... A01N/25/02 |
| WO | 98/18321 | | 5/1998 | .......... A01N/25/30 |
| WO | 98/31518 | | 7/1998 | ............ B27K/3/00 |

OTHER PUBLICATIONS

Hirobumi et al., Abstract, Bacterial detergent compositions: 120: 301698x. abstract of Japanese Patent Specification No. 05–311196 (Nov. 1993).

Archer et al., "Screening of Wood Preservatives: Comparison of the Soil–Block, Agar–Block, and Agar–Plate tests", Forest Products Journal, vol. 45, No. 1, pp. 86–89. (Jan. 1994).

"Amine Oxides", Encyclopedia of Chemical Technology, vol. 2, pp. 259–271. John Wiley & Sons Inc 1998 (no month).

American Wood Preservers' Association, P5– Waterborne Preservatives, 4–5, 1998. (no month).

Liu et al., 25$^{th}$ Annual Meeting of the International Research Group on Wood Preservation, Nusa Dua Bali, Indonesia, May 29, 1994–Jun. 3, 1994.

Nicholas et al., 28$^{th}$ Annual Meeting of the International Research Group on Wood Preservation, Whistler, Canada, May 25, 1997–May 30, 1997.

Williams et al., American Wood–Perservers' Association, 90:156–176, 1994. (no month).

* cited by examiner

Primary Examiner—Anthony Green
(74) Attorney, Agent, or Firm—Darby & Darby

(57) ABSTRACT

The present invention provides a composition comprising an amine oxide and an iodine containing biocide. Another embodiment of the present invention is a method for preserving and/or waterproofing a wood substrate by contacting the composition with the wood substrate.

23 Claims, No Drawings

AMINE OXIDE/IODINE CONTAINING BLENDS FOR WOOD PRESERVATION

This application claims the benefit of U.S. Provisional Application Serial No. 60/135,568, filed May 24, 1999.

FIELD OF THE INVENTION

This invention relates to wood preservative and waterproofing compositions containing an amine oxide and an iodine containing biocide.

BACKGROUND OF THE INVENTION

Mixtures of didecyldimethylammonium chloride (DDAC) and iodine containing biocides such as iodopropynylbutylcarbamate (IPBC), are currently used for treating wood to prevent the growth of stain causing fungi (see, e.g., U.S. Pat. No. 4,950,685). IPBC is known to be effective against fungi that cause structural and cosmetic damage to wood.

These mixtures are often distributed as concentrates. When diluted, the solutions frequently are characterized by poor phase and color stability, the IPBC often coming out of solution within a day or two after preparation. These solution also have low corrosion resistance. Furthermore, DDAC and IPBC compositions containing iron stain inhibitors typically have a low pH, making them less desirable for use in mills and other factories. A firer disadvantage of many of the prior art wood preservative compositions is that they contain halides, which are considered environmentally unfriendly.

Therefore, there is a need for iodine containing biocide compositions which have improved phase and color stability and corrosion resistance, and are able to form compositions containing iron stain inhibitors at higher pH.

SUMMARY OF THE INVENTION

Applicants have discovered that amine oxides enhance the performance of iodine-containing biocides as wood preservatives and provide waterproofing properties. The present invention provides a composition comprising an amine oxide and an iodine-containing biocide, particularly iodopropynyl butyl carbamate.

Another embodiment of the present invention is a method for preserving and/or waterproofing a wood substrate by impregnating the wood substrate with the composition.

Yet another embodiment is an article comprising a wood substrate treated with the composition of the present invention.

The composition of the invention has improved phase stability over prior art compositions and high resistance to color formation. The composition of the invention also has low corrosivity to metal components, including, but not limited to, steel components, such as those used in wood treatment systems. Compositions of the present invention which include iron stain inhibitors generally have higher pH than prior art iodine containing biocide containing compositions, allowing for safer handling of such compositions. Additionally, the amine oxide in the composition may impart waterproofing properties to the wood. Further, the composition of the present invention may be advantageously free of halide ions.

DETAILED DESCRIPTION OF THE INVENTION

Examples of compounds which may be used as the iodopropynyl component of the invention are the fungicidally active iodoalkynyl derivatives. These include compounds derived from propyne or iodopropynyl alcohols, such as the esters, ethers, acetals, carbamates and carbonates and the iodopropynyl derivatives of pyrimidines, triazolinones, tetrazoles, triazinones, sulfamides, benzothiazoles, ammonium salts, carboxamides, hydroxamates, and ureas.

Preferred iodine containing biocides include 3-iodo-2 propynyl derivatives such as 3-iodo-2-propynyl butyl carbamate, 3-iodo-2-propynyl succinate and p-chlorophenyl-3-iodopropynyl formal; an iodo sulfone derivative, or triiodoallyl alcohol.

The iodopropynyl carbamate compounds, included within the broadly useful class of compounds, have the generic formula:

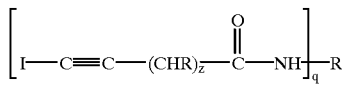

I wherein R is selected from the group consisting of hydrogen, and substituted and unsubstituted alkyl, aryl, and alkylaryl groups having from 1 to 20 carbon atoms; and q and z are independent integers from 1 to 3.

The iodopropynyl ester compounds are included within the broadly useful class of compounds having the generic formulas:

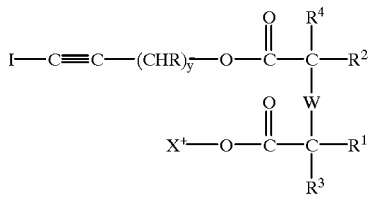

II and

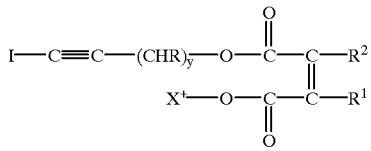

III wherein:

$R^1$ and $R^2$ are defined as $R^3$ and $R^4$ below or are joined to form a cycloalkyl, cycloalkenyl, aromatic or a heterocyclic ring containing an oxygen, nitrogen or sulfur atom or an alkoxy, amino, carboxyl, halo, hydroxyl, keto or a thiocarboxyl-substituted derivative thereof;

$R^3$ and $R^4$ are independently selected from (A) hydrogen, alkyl, cycloalkyl, alkenyl, cycloalkenyl, aryl, a heterocyclic ring containing an oxygen, nitrogen or sulfur atom, alkoxy, amino, carboxyl, halo, hydroxyl, keto or a thiocarboxyl and (B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl; y is 0 to 16; W may be a single bond, oxygen, $NR^5$, or $(CR^6R^7)_p$, wherein $R^5$ is hydrogen, alkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carboxyl, halo, hydroxyl, keto, or a thiocarboxyl wherein $R^6$ and $R^7$ are defined as $R^3$ and $R^4$ above; and p is an integer from 1 to 12. The above definition of $R^5$ includes, among other things, an aminoalkyl group.

The heterocyclic rings referred to in the above definitions may contain from 5 to 8 members, the alkyl or cycloalkyl groups from 1 to 18 atoms, the alkenyl or cycloalkenyl groups from 2 to 18 carbon atoms, and the aryl groups from 6 to 10 members. X is hydrogen or a salt-forming cation such as an alkali metal, an alkaline earth metal, ammonium, tertiary ammonium, a quaternary ammonium, a biguanide or a polybiguanide.

In formula III, when $R^1$ and $R^2$ are hydrogen, the compound is a maleate. When $R^1$ and $R^2$ are joined together to form part of a six membered aromatic ring the compound is a phthalate. In formula II, when $R^1$, $R^2$, $R^3$, and $R^4$ are hydrogen and W is a single bond, the compound is a succinate. When $R^1$, $R^2$, $R^3$ and $R^4$ are hydrogen and W is an oxygen, the compound is a diglycolate. Other compounds include the mono-iodopropynyl esters of anhydrides such as ethylenediamine tetraacetic dianhydride, 3,3-dimethylglutaric anhydride, S-acetylmercaptosuccinic anhydride, dichloromaleic anhydride, 2-dodecen-1-yl succinic anhydride and cis-5-norbornene-endo-2,3-dicarboxylic anhydride. Where hydrophilicity is desired, the sodium salts may be used because of their extremely high water solubility. Preferred carboxylic acid anhydrides include succinic, itaconic, phthalic, tetrachlorophthalic, and diglycolic anhydride. Such compounds are defined in U.S. Pat. No. 4,844,891 and 5,073,570.

More preferably the iodine containing biocide is 3-iodo-2-propynyl butyl carbamate (IPBC). The IPBC may be any grade of IPBC including, but not limited to, an essentially pure commercial grade IPBC in solid form and a commercially available 40% grade in a solvent.

The iodopropynyl compounds are also included within the class of compounds having the generic formula:

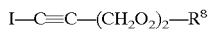

wherein $R^8$ is benzyl or benzyl substituted with a methyl, methoxy, carboxyl, halogen or nitro group; preferably the compound is p-chlorophenyl-3- iodopropynyl formal.

The amine oxide may be a trialkylamine oxide; an alkylcyclicamine oxide; a dialkylpiperazine di-N-oxide; an alkyldi(poly(oxyalkylene))amine oxide; a dialkylbenzylamine oxide; a fatty acylamidopropyldimethylamine oxide; a diamine oxide; a triamine oxide; and any combination of any of the foregoing.

Preferred trialkylamine oxides have the formula $R^9R^{10}R^{11}N{\rightarrow}O$, where $R^9$ is a linear, branched, cyclic or any combination thereof $C_6$ to $C_{40}$ saturated or unsaturated group; and $R^{10}$ and $R^{11}$ independently are linear, branched, or any combination thereof $C_1$ to $C_{40}$ saturated or unsaturated groups. $R^9$, $R^{10}$, and $R^{11}$ independently may be alkyl, alkenyl, or alkynyl groups; or may be replaced by other short chain alkyl or substituted alkyl groups, such as ethyl and hydroxyethyl. More preferably, $R^9$ is a linear, branched, cyclic or any combination thereof $C_8$ to $C_{22}$ saturated or unsaturated group, such as coco, hydrogenated tallow, soya, decyl, and hexadecyl; and $R^{10}$ and $R^{11}$ independently are linear, branched, or any combination thereof $C_1$ to $C_{22}$ saturated or unsaturated groups, such as coco, hydrogenated tallow, soya, decyl, and hexadecyl.

A preferred trialkylamine oxide is a dialkylmethylamine oxide having the formula $R^9R^{10}CH_3N{\rightarrow}O$, where $R^9$ and $R^{10}$ are defined as above. Another preferred trialkylamine oxide is an alkyldimethylamine oxide having the formula $R^9(CH_3)_2N{\rightarrow}O$, where $R^9$ is defined as above. Suitable alkyldimethylamine oxides include, but are not limited to, a $C_{10}$alkyldimethylamine oxide, a $C_{12}$–$C_{14}$, alkyldimethylamine oxide, a $C_{16}$–$C_{18}$ alkyldimethylamine oxide, and any combination of any of the foregoing.

Preferred alkylcyclicamines oxide have the formula $R^{12}R^{13}R^{14}N{\rightarrow}O$ where $R^{12}$ is defined as $R^9$ above and $R^{13}$ and $R^{14}$ are linked to form a cyclic group. The cyclic group typically contains from about 4 to about 10 carbon atoms and may optionally contain oxygen, sulfur, nitrogen, or any combination of any of the foregoing. More preferred alkylcyclicamine oxides include, but are not limited to, an alkylmorpholine N-oxide, a dialkylpiperazine di-N-oxide, and any combination of any of the foregoing.

Preferred alkylmorpholine N-oxides have the formula

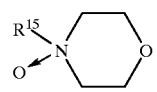

where $R^{15}$ is defined as $R^9$ above.

Preferred dialkylpiperazine di-N-oxides have the formula

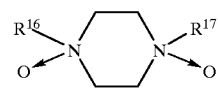

where $R^{16}$ is defined as $R^9$ above and $R^{17}$ is defined as $R^{10}$ above.

Preferred alkyldi(poly(oxyalkylene))amine oxides have the formula

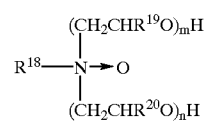

where $R^{18}$ is defined as $R^9$ above; $R^{19}$ and $R^{20}$ independently are H or $CH_3$; and m and n independently are integers from about 1 to about 10.

Preferred dialkylbenzylamine oxides have the formula $R^{21}R^{22}R^{23}N{\rightarrow}O$, where $R^{21}$ is defined as $R^9$ above; $R^{22}$ is defined as $R^{10}$ above; and $R^{23}$ is benzyl. More preferred dialkylbenzylamine oxides include, but are not limited to, alkylbenzylmethylamine oxides having the formula $R^{21}R^{23}CH_3N{\rightarrow}O$ where $R^{21}$ and $R^{23}$ are defined as above.

Preferred fatty acylamidopropyldimethylamine oxides have the formula

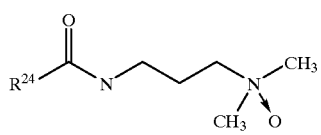

where $R^{24}$ is defined as $R^9$ above.

Preferred diamine oxides have the formula

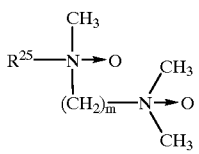

where $R^{25}$ is defined as $R^9$ above; and m is an integer from about 1 to about 10.

Preferred triamine oxides have the formula

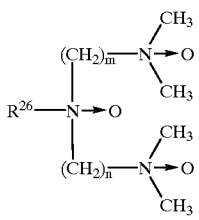

where $R^{26}$ is defined as $R^9$ above; and m and n independently are integers from about 1 to about 10.

Long chain ($C_{16}$ or greater) amine oxides, such as hexadecyldimTethylamine oxides, octadecyldimnethylamnine oxides and hydrogenated tallow amine oxides, are particularly preferable for imparting waterproofing properties to the composition. Short chain ($C_{14}$ and shorter) amine oxides, such as decyldimethylamnine oxides, lauryldimethylamine oxides and tetradecyldimnethylamine oxides, aide in solubilizing the IPBC and long chain amine oxides, and are efficient stabilizers.

A blend of long chain and short chain amine oxides is also contemplated in one embodiment of the present invention. The long chain amine oxides may be blended with the short chain amine oxides in a ratio of about from about 1:10 to 10:1 in order to yield a clear and stable preservative solution as described herein upon dissolution of iodine containing biocide in the amine oxide solution. For example, in a preferred embodiment, a mixture of long chain (e.g., $C_{16}$) and short chain (e.g., $C_{12}$) amine oxides in a ratio of 5:2 provides the desired dissolution of iodine containing biocide to provide a clear and stable solution. The appropriate ratio of long to short chain amine oxides can be readily determined by those of skill in the art using methods provided herein to test solubility and stability of the solutions.

The composition may include a solvent, such as water and water miscible solvents, including, but not limited to, alcohols, such as ethanol, glycols, esters, ethers, polyethers, amines, and any combination of any of the foregoing.

The composition, when in concentrated form, preferably contains from about 20 to about 70% by weight, and preferably from about 30 to 65% by weight, of combined amine oxide and iodine containing biocide based upon 100% weight of total composition. The concentrate contains 0.01 to 1 parts of iodine containing biocide per part of amine oxide; and most preferably 0.05 to 0.5 parts of iodine containing biocide to 1 part amine oxide.

The concentrate may be diluted to a range of about 0.1 to 5% (total solids) for treating wood. Use dilutions of the composition typically comprise a biocidally effective amount of iodine containing biocide and a preservative enhancing and/or waterproofing effective amount of the amine oxide. Use dilutions preferably comprise from about 0.5 to about 2.0% by weight of amine oxide and from about 0.05 to about 0.2% by weight of iodine containing biocide based upon 100% weight of total composition. The composition of the invention has a weight ratio of iodine containing biocide to amine oxide of about 0.001:1, preferably 0.01:0.8.

Iron stain inhibitors, such as phosphonic acid derivatives, may be included in the composition. Suitable phosphonic acid derivatives include, but are not limited to, amino tri(methylenephosphonic acid), 1-hydroxyethylidene-1,1-diphosphonic acid (HEDP), diethylenetriaminepenta (methylene-phosphonic acid), bis hexamethylene triamine phosphonic acid, and any combination of any of the foregoing. The iron stain inhibitor will be present in an amount of about 0.01 to 1%, preferably in an amount of about 0.05 to 0.5%, and most preferably in an amount of about 0.1 to 0.4%. Typically, the pH of the composition containing the iron stain inhibitor will be in the range of about 3.0 to 7.0, and preferably about 3.8 to 5.2.

Other adjuvants may be included in the composition as known to one of ordinary skill in the art. Other biocides, fungicides and insecticides may be include in the composition.

The composition of the present invention is readily prepared by mixing iodine containing biocide, amine oxide, solvents, and adjuvants. The mixture may be heated and/or stirred to expedite mixing.

Another embodiment of the present invention is a method for preserving and/or waterproofing a wood substrate by contacting a wood substrate with the composition of the present invention. The composition may be applied by any wood treating method known to one of ordinary skill in the art including, but not limited to, brushing, dipping, soaking, vacuum impregnation (e.g., double vacuum technique), and pressure treatment using various cycles.

The following examples illustrate the invention without limitation. All parts and percentages are given by weight unless otherwise indicated.

Example 1

These experiments were performed to compare the solubility and stability of compositions of the invention to the prior art. The following solutions were prepared:

(A) 3.8 g of iodopropynyl butyl carbamate (IPBC) was dissolved in 100 g of 30% cocodimethylamine oxide in water (Barlox® 12, Lonza Inc., Fair Lawn, N.J.) by warming and/or stirring to form a concentrate containing about 29% cocodimethylamine oxide and about 3.7% IPBC. The weight ratio of cocodimethylamine oxide to IPBC was about 8:1. This concentrate, a faint yellow clear liquid, remained unchanged upon storage at ambient conditions for at least 20 months.

(B) 3.4 g of the above IPBC/cocodimethylamine oxide concentrate was diluted in 100 g of water to form a use-dilution containing about 1% cocodimethylamine oxide and about 0.125% IPBC.

(C) A second IPBC/cocodimethylamine oxide use-dilution containing an iron-stain inhibitor was prepared by adding 0.25% hydroxyethylidene diphosphonic acid (HEDP) to the use-dilution of Sample (B).

(D) 1 g of IPBC, 10 g of an 80% aqueous solution of didecyldimethylammoniumchloride (DDAC) (Bardac® 2280, Lonza Inc., Fair Lawn, N.J.) and 17 g of water were mixed and stirred. The resulting concentrate contained about 28.5% DDAC and about 3.6% IPBC. The weight ratio of DDAC to IPBC was about 8:1. 3.5 g of this IPBC/DDAC solution was diluted in 100 g of water to form a use-dilution containing about 1% DDAC and about 0.125% IPBC.

(E) A second IPBC/DDAC use-dilution was prepared by adding 0.25% HEDP to the use-dilution of Sample (D).

(F) 50 parts of hexadecyldimethylamine oxide (Barlox 16S, Lonza Inc., Fair Lawn, N.J.), 20 parts of Barlox 12, 80 parts of water, and 2.6 parts of IPBC solid were mixed and warmed to give a clear solution.

(G) 5 g of a Barlox 12 preparation (65% active cocodimethylamine oxide in 20% ethanol and 15 % water) was mixed with 0.4 g IPBC. The mixture was allowed to stand with occasional shaking at room temperature to effect complete dissolution of the solid. The resulting concentrate contained 60% amine oxide and 7.4 % IPBC.

(H) A use-dilution was prepared by dissolving 1.7 g of concentrate (G) in 98.3 g of water, to yield a solution containing 1.0% cocodimethylamine oxide and 0.15% IPBC.

A dispersion of IPBC in water was prepared by dissolving 0.125 g of IPBC in 1 g of ethanol and mixing this solution with 99 g of water. The resulting solution contained about 0.125% IPBC, which was not soluble and separated rapidly on standing. Results of solution aging are given in Table 1:

TABLE 1

| Test Material | Component Ratios | Total Solids % | Solution Observations Shortly after preparation | pH | After 20 months standing | pH |
|---|---|---|---|---|---|---|
| A $C_{12}AO$/ IPBC | 8-1 | 32.5 | Faint yellow clear fluid liquid | — | Faint yellow clear fluid liquid | — |
| B $C_{12}AO$/ IPBC | 8-1 | 1.125 | Clear white solution | 7.1 | Clear white solution | 6.9 |
| C $C_{12}AO$/ IPBC HEDP | 8-1 | 1.125 0.25 | Clear light solution | 3.9 | Light yellow clear solution | 3.3 |
| D DDAC/ IPBC | 8-1 | 1.125 | White solid separated | 5.1 | Cloudy yellow solid separated | 2.9 |
| E DDAC/ IPBC HEDP | 8-1 | 1.125 0.25 | Light yellow hazy | 2.6 | Hazy separation | 2.3 |
| F $C_{16}AO$/ $C_{12}AO$/ IPBC | 5.7-2.3-1 | 1.125 | Clear light solution | 7.0 | — | |
| G $C_{12}AO$/ IPBC | 8-1 | 67.4 | Faint yellow clear fluid liquid | — | — | — |
| H $C_{12}AO$/ IPBC | 8-1 | 1.15 | Clear colorless solution | 7.5 | — | — |

The solution of the invention prepared with the amine oxide (solution B) remained in solution and was stable for at least 20 months. The IPBC with DDAC (solution D), the composition of the prior art, initially remained in solution but within hours separated out of solution. The DDAC/IPBC solution turned yellow and the pH dropped, suggesting decomposition.

The solution containing the amine oxide and the iron stain inhibitor HEDP (solution C) had a higher (safer) pH, compared to the DDAC and HEDP containing solution (solution E). Further, the amine oxide/HEDP solution remained a stable clear solution, whereas the DDAC/HEDP solution showed some separation.

The concentrate prepared with up to 60% of solids and ethanol (G) remained in solution and the use solution prepared therefrom also remained in solution after preparation.

EXAMPLE 2

These experiments were performed to compare the wood preserving properties of IPBC dissolved in solution by amine oxide and IPBC dispersed by DDAC, or dispersed alone in water.

The solutions prepared in Example 1 were tested for efficacy in controlling the growth of natural stain organisms on white birch. White birch tree branches, 3" in diameter and 6" in length, were cut into four sections. The inner bark was left on the pieces. A white birch piece was dipped into a test solution for 1 minute, placed in a sealed clear plastic bag, and stored at ambient conditions. The piece was observed after 1 week, 3 weeks, 7 weeks, and 12 weeks for the growth of stains, molds, and fungi. The results are shown in Table 2 below.

TABLE 2

| | Rating of Fungal Growth on White Birch | | | |
|---|---|---|---|---|
| Solution | 1 Week | 3 Weeks | 7 Weeks | 12 Weeks |
| None | 1 | 1 | 1 | — |
| Water | 4 | 2 | 1 | — |
| 0.125% dispersion of IPBC | 3 | 4 | 3 | 2 |
| 0.125% IPBC/1% cocodimethylamine oxide (solution B) | 4 | 4 | 4 | 3 |
| 0.125% IPBC/1% DDAC (solution D) | 4 | 4 | 4 | 4 |

Rating Scale: 1 - Heavy fungal growth

2—Black and/or white fungal growth visible on all faces and ends

3—Trace amount of white/black fungal growth

4—Clean surface with no visible stain or mold

The results in Table 2 show that birch wood samples treated with the composition of the invention (solution B) protected the wood against stains and growth of molds as well as the prior art composition D (IPBC/DDAC).

In a second series, a piece of green chestnut oak wood was cut into pieces and dipped into test solutions. This series included one solution with the iron stain inhibitor (bis-(hexamethylene)triamine phosphonic acid (Unihib® 1704, Lonza Inc., Fair Lawn, N.J.). The results are in Table 3. The ratings are as in Table 2 above.

TABLE 3

| | Rating of Fungal Growth on Oak | | | |
|---|---|---|---|---|
| Treatment | 2 Weeks | 4 Weeks | 5 Weeks | 9 Weeks |
| None | 1 | 1 | | |
| Water dip | 2 | 2 | 1 | |
| 1% $C_{12}AO$/0.125% IPBC (solution B) | 4 | 3 | 2 | 2 |
| 1% DDAC/0.125% IPBC (solution D) | 3 | 3 | 2 | 1 |
| 1% $C_{12}AO$/0.125% IPBC + 0.2% bis-(hexamethylene)triamine phosphonic acid | 4 | 3 | 3 | 2 |
| IPBC in ethanol/water | 4 | 3 | 2 | 2 |

The amine oxide protected the wood from fungal growth for several weeks, further demonstrating the enhancing effect of this component.

EXAMPLE 3

Solutions prepared as described in Example 1 were tested on agar plates for their ability to inhibit or retard fungal growth. The solutions were tested using standard methods (see e,g, Archer et al., Forest Products Journal, 1995, 45:86–89) against the white rot fungus *Trametes versicolor*; the brown rot fungus *Gloephyllum trabeum*, which is particularly tolerant of arsenic and phenolic type wood preservatives; a brown rot fungus *Poria placenta*, which is tolerant of copper wood preservatives; and the soft rot fungus *Chaetomium globosum*. The concentration at which 50% retardation of the growth of each fungus occurred, which is defined as the $IC_{50}$ value, was determined for each solution. The results are shown in Table 4 below.

TABLE 4

| | $IC_{50}$ (ppm) | | | |
| --- | --- | --- | --- | --- |
| Solution | T. versicolor | G. trabeum | P. placenta | C. globosum |
| IPBC in water | 8 | 1.5 | 0.8 | 4 |
| 1% $C_{12}$AO/0.125% IPBC (solution B) | 1.5 | 1 | 1.3 | 4 |
| 1% DDAC/0.125% IPBC (solution D) | 10 | 0.8 | 1 | 4 |

The results indicate that the biological efficacy of the IPBC in the presence of amine oxide (solution B) is the same or better than IPBC alone or in the prior art combination (solution D).

EXAMPLE 4

The corrosivity of solutions containing IPBC/DDAC or IPBC/amine oxide was compared. Carbon steel coupons were three-quarters covered with the test solutions shown in Table 5 for 3 weeks, with occasional shaking to periodically wet the top of the coupon. After 3 weeks, each coupon was observed and the percent weight lost was determined. The results are shown below in Table 5:

TABLE 5

| Solution* | Percent Weight Lost | Observations on Corrosion |
| --- | --- | --- |
| 0.15% IPBC in Water | 0.3 | Solution rusty and coupon rust colored especially in the liquid |
| 0.08% IPBC/0.65% DDAC in water | 0.4 | Corrosion |
| 0.12% IPBC/1% DDAC | 0.4 | Rusty to dark solution; More corrosion visible than at lower concentration |
| 0.08% IPBC/ 0.65% cocodimethylamine oxide | 0.2 | Clear initially then rusty spots forming |
| 0.12% IPBC/ 1% cocodimethylamine oxide | 0 | Unchanged for several days, then traces of corrosion forming on edges of the coupon |
| 0.1% IPBC/ 3:5 blend of $C_{10}$-$C_{18}$ amine oxides | 0.1 | Unchanged for several days, then traces of corrosion forming on edges of the coupon |

% by weight

As noted in Table 5, the mixture of IPBC and water corroded the carbon steel, causing a rusty appearance and loss of a portion of the coupon. The prior art IPBC/DDAC solution also corroded the coupons. The amine oxide containing composition of the present invention decreased the amount and rate of corrosion of the steel coupon.

EXAMPLE 5

The following experiments were performed to evaluate the waterproofing properties of the compositions of the present invention.

Samples of Ponderosa pine were treated with the test solutions prepared in Example 1 using a double vacuum method. Each wood sample was evacuated in a vacuum desiccator to about −80 kPa pressure. A test solution was injected into the chamber and the vacuum was released with air. Excess solution was blotted from the wood sample and the wood was returned to the desiccator on a small rack. Vacuum was drawn again to remove liquid from the wood ("kickback" solution). Samples that were subjected to weathering were placed on a flat surface outside and exposed to natural environmental weather conditions for 90 days.

The results are shown in Table 6.

TABLE 6

| | Water Uptake % in 30 Minutes Soak | |
| --- | --- | --- |
| Treating Compositions | Freshly Treated | 90 Days Weathering |
| Untreated Control | 75 | 89 |
| $C_{12}$AO/IPBC (solution B) | 51 | 63 |
| DDAC/IPBC (solution D) | 62 | 73 |
| $C_{16}$AO/$C_{12}$AO/IPBC (solution F) | 43 | 43 |

The use of IPBC with a blend of amine oxides (solution F) provided a treating composition with good waterproofing properties; both freshly treated wood and wood after weathering took up less water than the other test combinations.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A water stable wood preservative composition comprising an amine oxide in a preservative enhancing and/or waterproofing effective amount, wherein the amine oxide is a trialkylamine oxide, an alkylcyclicamine oxide, a dialkylpiperazine di-N-oxide, an alkyldi(ethoxylated oxyalkyl) amine oxide, a dialkylbenzylamine oxide, a fatty dimethylaminopropylamine oxide, a diamine oxide, a triamine oxide, or any combination of any of the foregoing; and an iodine containing biocide in a biocidally effective amount, wherein the iodine is covalently bonded to carbon.

2. The composition of claim 1, wherein the weight ratio of said iodine containing biocide to said amine oxide is about 0.001:1.

3. The composition of claim 1, wherein said composition is a use dilution comprising from about 0.5 to about 2% by weight of amine oxide and from about 0.05 to about 0.2% by weight of iodine containing biocide based upon 100% weight of total composition.

4. The composition of claim 1, wherein said trialkylamine oxide has the formula $R^9R^{10}R^{11}N\rightarrow O$, wherein $R^9$ is a linear, branched, cyclic or any combination thereof $C_6$ to $C_{40}$ saturated or unsaturated group; and $R^{10}$ and $R^{11}$ independently are linear, branched, or any combination thereof $C_1$ to $C_{40}$ saturated or unsaturated groups.

5. The composition of claim 4, wherein $R^9$ is $C_8$ to $C_{22}$; and $R^{10}$ and $R^{11}$ independently are $C_1$ to $C_{22}$.

6. The composition of claim 4, wherein said trialkylamine oxide is an alkyldimethylamine oxide having the formula $R^9(CH_3)_2N\rightarrow O$, wherein $R^9$ is $C_6$ to $C_{40}$.

7. The composition of claim 6, wherein $R^9$ is $C_8$ to $C_{22}$.

8. The composition of claim 6, wherein said alkyldimethylamine oxide is a $C_{10}$ alkyldimethylamine oxide, $C_{12-C14}$ alkyldimethylamine oxide, $C_{16-C18}$ alkyldimethylamine oxide, or any combination of any of the foregoing.

9. The composition of claim 8, wherein said alkyldimnethylamine oxide is a blend of $C_{16}$–$C_{18}$ alkyldimethylamine oxides and $C_{12-C14}$ alkyldimethylamine oxides in a ratio of about 5 to 2.

10. The composition of claim 9, wherein the $C_{16}$–$C_{18}$ alkyldimethylamine oxide is a hexadecyldimethylamine oxide, octadecyldimethylamine oxide or an hydrogenated tallow amine oxide.

11. The composition of claim 9, wherein the $C_{12-C14}$ alkyldimethylamine oxide is a decyldimethylamine oxide, lauryldimethylamine oxide or tetradecyldimethylamnine oxide.

12. The composition of claim 1, wherein the iodine containing biocide is an iodopropynyl derivative of the formula

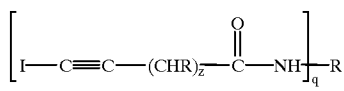

I wherein R is hydrogen or a substituted or unsubstituted alkyl, aryl, or alkylaryl group having from 1 to 20 carbon atoms; and z and q are independent integers from 1 to 3.

13. The composition of claim 1, wherein the iodine containing biocide is an iodopropynyl derivative of the formula

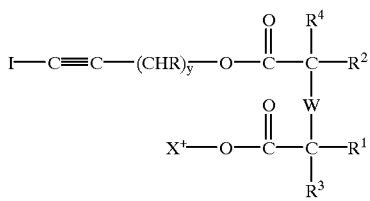

II or

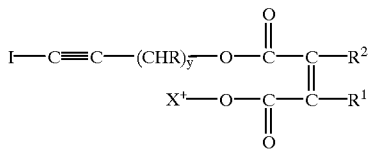

III wherein $R^1$ and $R^2$ are defined as $R^3$ and $R^4$ below or are joined to form a cycloalkyl, cycloalkenyl, aromatic or a heterocyclic ring containing an oxygen, nitrogen or sulfur atom or an alkoxy, amino, carboxyl, halo, hydroxyl, keto or a thiocarboxyl-substituted derivative thereof; $R^3$ and $R^4$ are independently selected from (A) hydrogen, alkyl, cycloalkyl, alkenyl, cycloalkenyl, aryl, a heterocyclic ring containing an oxygen, nitrogen or sulfur atom, alkoxy, amino, carboxyl, halo, hydroxyl, keto or a thiocarboxyl and (B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl; y is 0 to 16; W is a single bond, oxygen, $NR^5$, or $(CR^6R^7)p$, wherein $R^5$ is hydrogen, alkyl, aminoalkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carboxyl, halo, hydroxyl, keto, or a thio-carboxyl wherein $R^6$ and $R^7$ are defined as $R^3$ and $R^4$ above and p is an integer from 1 to 12; and wherein the heterocyclic rings comprise from 5 to 8 members, the alkyl or cycloalkyl groups from 1 to 18 atoms, the alkenyl or cycloalkenyl groups from 2 to 18 carbon atoms, and the aryl groups from 6 to 10 members.

14. The composition of claim 12, wherein the iodopropynyl compound is a 3-iodo-2-propynyl derivative.

15. The composition of claim 14, wherein the 3-iodo-2-propynyl derivative is 3-iodo-2-propynyl butyl carbamate, 3-iodo-2-propynyl succinate or p-chlorophenyl-3-iodopropynyl formal.

16. The composition of claim 15, the 3-iodo -2-propynyl derivative is 3-iodo-2-propynyl butyl carbamate.

17. The composition of claim 1, further comprising a solvent.

18. The composition of claim 17, wherein said solvent is water, an alcohol, a glycol, an ester, an ether, a polyether or any combination of any of the foregoing.

19. The composition of claim 1, further comprising a phosphonic acid derivative in an amount effective to inhibit iron staining.

20. The composition of claim 19, wherein said phosphonic acid derivative is amino tri(methylenephosphonic acid), 1-hydroxyethylidene-1,1-diphosphonic acid, diethylenetriaminepenta(methylene-phosphonic acid), bis hexamethylene triamine phosphonic acid, or any combination of any of the foregoing.

21. The composition of claim 20, wherein the phosphonic acid derivative is present in an amount of about 0.01 to 1%.

22. A method for preserving a wood substrate, said method comprising contacting said wood substrate with the composition of claim 1.

23. A method for waterproofing a wood substrate, said method comprising contacting said wood substrate with the composition of claim 1.

* * * * *